United States Patent [19]

Kirschen

[11] Patent Number: 4,804,261
[45] Date of Patent: Feb. 14, 1989

[54] ANTI-CLAUSTROPHOBIC GLASSES

[76] Inventor: David G. Kirschen, 1622 N. Mountain View Pl., Fullerton, Calif. 92631

[21] Appl. No.: 30,587

[22] Filed: Mar. 27, 1987

[51] Int. Cl.⁴ .............................................. G02C 7/14
[52] U.S. Cl. ...................................... 351/158; 351/50
[58] Field of Search ...................... 351/50, 57, 158, 86; 350/638; 248/471

[56] References Cited

U.S. PATENT DOCUMENTS

| | | | |
|---|---|---|---|
| 2,502,224 | 3/1950 | Kozloff | 351/50 |
| 2,819,650 | 1/1958 | Seron | 351/156 |
| 3,045,544 | 7/1962 | Schmidt | 351/57 |
| 3,450,467 | 6/1969 | Phillips | 351/156 |
| 4,196,982 | 4/1980 | Watkins | 351/86 |
| 4,338,004 | 7/1982 | Vosper | 351/86 |
| 4,647,165 | 3/1987 | Lewis | 351/57 |

FOREIGN PATENT DOCUMENTS

| | | | |
|---|---|---|---|
| 2532070 | 2/1984 | France | 351/50 |
| 2764 | of 1886 | United Kingdom | 351/50 |

*Primary Examiner*—Rodney B. Bovernick
*Assistant Examiner*—Jay Ryan
*Attorney, Agent, or Firm*—Marvin H. Kleinberg

[57] ABSTRACT

A unique mirror optical system reduces the anxiety of patients due to claustrophobia during magnetic resonance imaging or the like. A back surface mirror is mounted on a spectacle frame which is attached to the patient's head with an adjustable elastic band. With the patient in the supine position, the mirror allows the patient to see over the head or feet to scenes placed on a distant surface. Since the patient can see "out", the confined feeling which triggers the claustrophobia response is greatly reduced or eliminated.

11 Claims, 2 Drawing Sheets

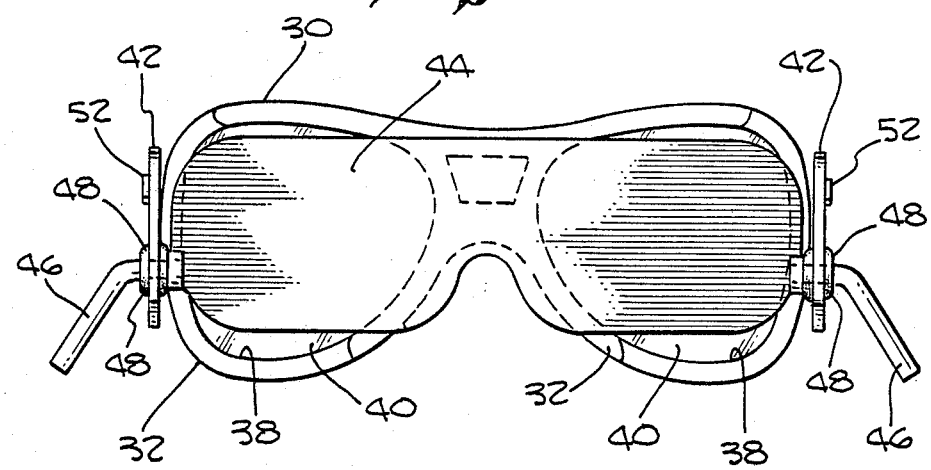
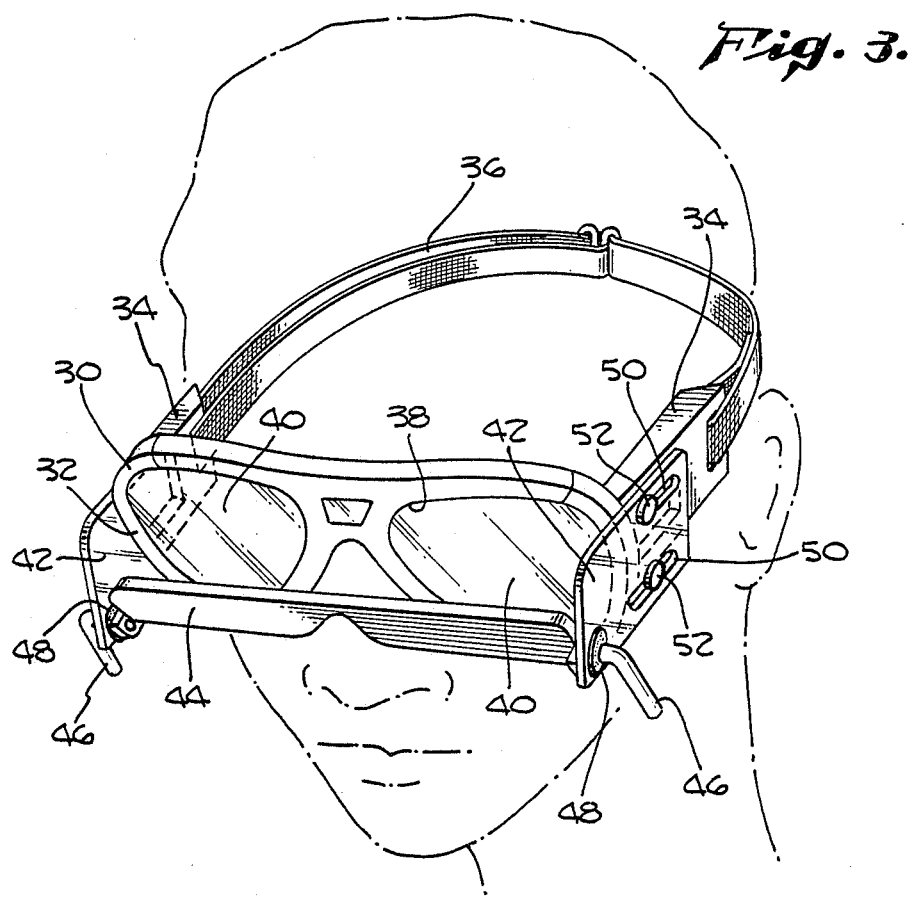

ANTI-CLAUSTROPHOBIC GLASSES

BACKGROUND OF INVENTION

The invention relates to mirror optical systems and more specifically to a mirror which can be worn by patients while undergoing various medical procedures.

Magnetic Resonance Imaging (MRI) is a radiologic technique which allows the viewing of internal human structures without the use of ionizing radiation. The technique works by placing the patient's body in a strong magnetic field and taking serial photographs using magnetic imaging techniques. In order to create the strong magnetic field necessary for this technique, a very large electro-magnet must be used. The commercial devices for this purpose currently in use can measure up to 15 feet wide, 10 feet high, and 7 feet deep. In the middle of this large mass is a cylindrical bore generally no greater than 2 feet in diameter The patient is placed from head to toe in this bore for the duration of the scan. The size and massiveness of these devices is very upsetting to many patients especially since the patient is wholly surrounded by the apparatus.

Once the magnetic imaging process begins, the patient must lie perfectly still for a very long period of time. The average scan can last from 40 minutes to 1½ hours. Some patients try to close their eyes and sleep through the procedure. If they awaken during the scan, they can easily become disoriented because of the confining nature of the apparatus, and this can trigger a claustrophobia response. It has been estimated that between 5 and 10 percent of all patients who need this medical procedure cannot be successfully scanned because of claustrophobia.

Several techniques have been tried to alleviate this problem. Sedation is sometimes used to calm patients before the procedure. This technique has met with limited success but has several serious drawbacks. Sedation is a medical procedure requiring a physician's prescription and monitoring of the patient is required. If sufficient sedation is given to render the patient unconscious, close monitoring of the patient's vital signs must be done at regular intervals, which is generally impractical since the sensors will affect the scan. Sedation for extended periods is difficult to control and many patients are poor medical risks for sedation. If sedation is used, the procedure becomes much more costly because the scan which normally requires only a medical technologist to perform would also require an attending physician.

Sleep masks or blinders have been tried to alleviate the patient's anxiety. This technique has very poor patient acceptance for several reasons. First, the claustrophobic response begins before the patient enters the scanner. If blinders, which prevent all vision, were placed on the patient before entering the scanner the patient would be functionally blind and have to be led to the scanner, helped up onto the table and positioned. Patients are very disturbed if they are rendered blind, during a medical procedure. Second, a patient sleeping with the blinders on tends to move the body when sleeping, thereby interfering with the scanning procedure. If the patient then awakens and "sees" only blackness, the patient gets very disoriented especially if elderly and can not remember where he or she is. The patient can become very frightened and seriously disturbed under these conditions.

Another technique which is sometimes used is to have a trained person sit in the scanner room and talk to the patients during the scan, so that the patient will not feel "abandoned" in the scanner. The patient can not talk back for the duration of the scan since that will induce movement, especially if the head is being scanned. This is a very labor intensive method as it requires an extra person present during the entire procedure.

An optical device has been used by one scanner company in an attempt to combat the claustrophobia problem. A mirror is mounted in the head coil unit, angled such that the patient can see forward through the scanner towards his/her feet. There are a number of limitations to this device. First, it is only useful on the scanner unit of the particular manufacturer. Second, it can only be used when the head is being scanned. It is not useful when other parts of the body are being examined. Finally, the angle of the mirror which is fixed and non-movable, aims the patient's line of vision towards his/her feet. Viewing in this direction is difficult for many patients. If the patient has a large nose, large chest or breasts, a large abdomen, or large feet, they will not be able to see out the scanner beyond these anatomical features. Also, when positioned in the scanner, looking toward the feet makes the patient look forward through the scanner tunnel which emphasizes that the patient is in a confined space, thereby triggering a claustrophobia response.

Other commercially available optical devices, such as prism glasses, which have been used for bed-ridden patients, can not be used because they are made with various types of ferrous metals which are magnetically active. No object containing ferrous metals can be in the scanner room because they could create a hazard by being projected across the room by the strong magnetic field or because they can cause testing artifacts to appear on the scanning film.

What is needed is a device which allows patients to see outside the confines of the scanning unit, thereby reducing their anxiety. The device must be magnetically inert, that is, contain no ferrous metal, be light weight, and adjustable for many face sizes. It must be compact enough to fit inside the head coils of existing scanners and yet be large enough to give a good field of view. The needed device should be able to be used with most brands of scanners and be able to be used with body scans as well as scans of the head.

The present invention corrects many of the flaws of previous devices and techniques and provides an elegantly simple solution to a very persistent, costly, and complex problem. According to the present invention a mirror optical system is made of magnetically inert plastic and nylon parts and is sized to fit large and small heads alike. The system is light weight and comfortable to wear.

The system is used in the following way. The patient is seated on the scanner table and is asked to put on an optical device which fits much like a pair of glasses. An elastic band is adjusted to fit the patient's head loosely. The patient then lies down on the scanner table on his/her back and the angle of the mirror is adjusted so the patient can see straight back through the scanner. For scanners in which the patient is inserted head first and which is not open at both ends, the mirror can be adjusted to look forward, toward the feet and out of the scanner.

A technician walks into the field of view of the mirror and establishes verbal and eye contact with the patient by looking through the bore of the magnet and into the mirror. As the patient's body enters the scanner, the patient is unaware he/she is entering a confined space because attention is being directed out of the scanner. The technician then directs the patient's attention to a target or scene on the wall behind the scanner (usually a travel poster) and asks the patient to concentrate on a particular aspect of the scene. Once the patient's attention has been directed out of the scanner by using the invention, the scan can proceed.

One of the novel features of this invention is that first quality ophthalmic lenses are supplied with the device and are easily snap fitted into place. If a patient normally wears glasses, they can feel very uneasy or disoriented when they are asked to remove their glasses. With this device, lenses, which are close to the patient's prescription, can easily be placed in the frame by the technician, so when the patient is lying in the scanner looking into the optical device, he/she will be able to see the target clearly.

The design, construction, and use of this new device addresses many of the limitations and drawbacks to the solutions tried previously. The device requires no sedation. This optical device is designed to be used with fully awake and alert patients. If, however, a patient chooses to close his/her eyes and sleep, the device can still be used because, upon awakening and opening the eyes, patients will experience little or no disorientation because they will be looking at a familiar scene.

If a physician chooses to use a mild sedative with a patient for medical reasons, the device can still be used. Use of the glasses might have the advantage of reducing the dosage of the sedative used.

This invention also has many advantages over the sleep mask blinders. The patients do not have to be led into the scanning room and therefore the patient can establish good eye contact and rapport with the scanning technologist. There is little or no disorientation because the patients have their eyes open and are looking through glasses with lenses that are close to their own prescription. If they sleep during the scan, when they awaken they can reorient themselves visually because they have a familiar visual scene at which to look.

This device offers many improvements over devices currently marketed by a scanner manufacturer. First of all this device may be used with all MRI units, not just those manufactured by one company. Secondly, the mirror on the new invention is moveable. The angle can be changed to view down to the feet, like the existing unit or up over the head, which is the recommended orientation. The glasses can be used with both the head coil and the body scanner. Moreover, the glasses come with easily interchangeable prescription lenses so the patient can see clearly what is being presented in the mirror. In the existing unit, the patient's glasses must be removed.

The novel features which are believed to be characteristic of the invention, both as to organization and method of operation, together with further objects and advantages thereof will be understood better from the following description considered in connection with the accompanying drawings in which the preferred embodiment of the invention is illustrated by way of example. It is to be expressly understood, however, that the drawings are for the purpose of illustration and description only and are not intended as a definition of the limits of the invention.

DESCRIPTIONS OF THE EMBODIMENTS

FIG. 2 is front view of the anti claustrophobic goggles according to the present invention; and FIG. 3 is a perspective side view of the goggles of FIG. 1 with the mirror element at an angle to redirect vision.

Figure 1:
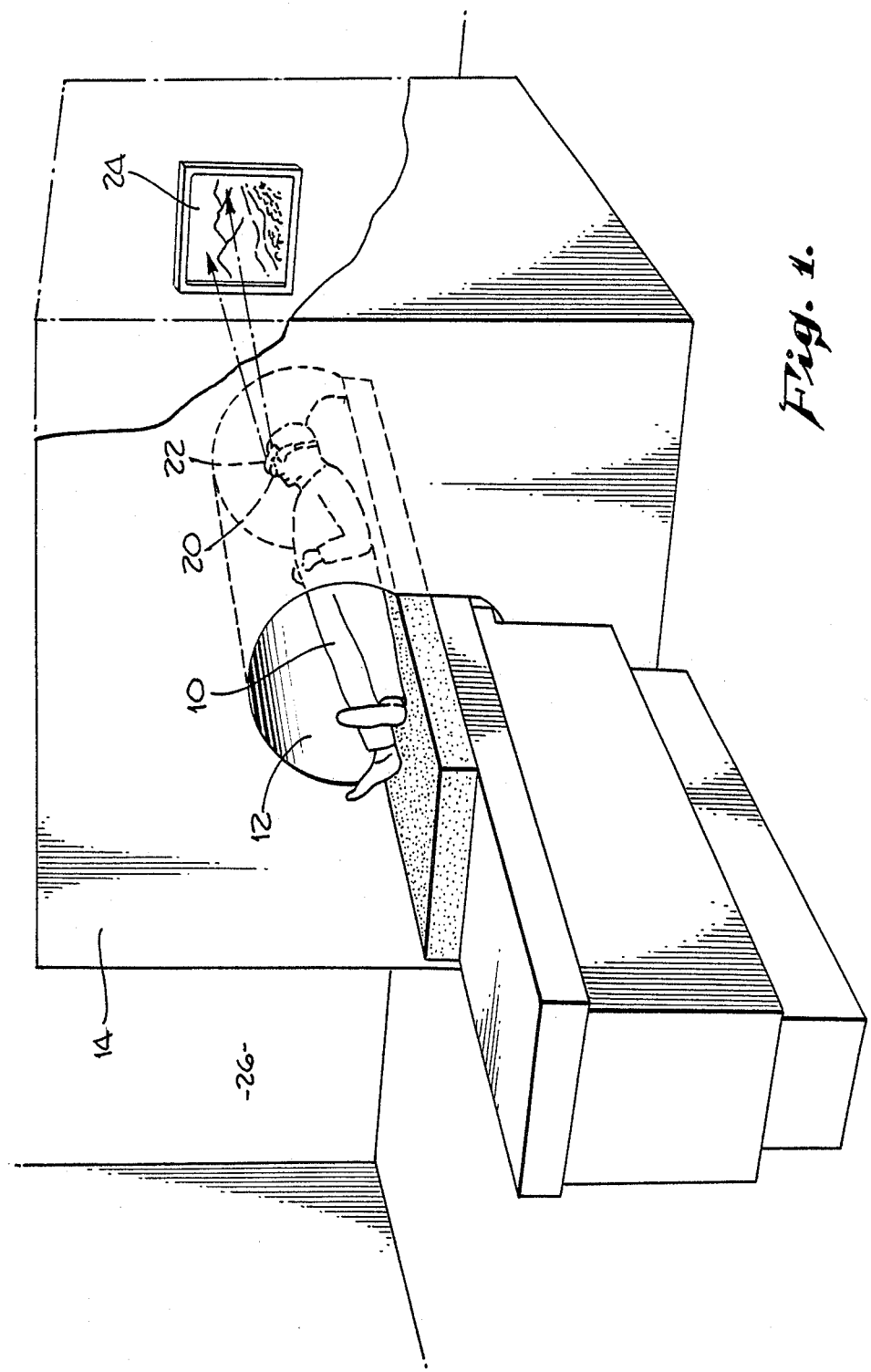
FIG. 1 is a perspective, shadow view showing a patient wearing a preferred embodiment of the present invention in a scanning device.

Turning first to FIG. 1, there is shown in phantom view, a supine patient 10 in the scanning cavity 12 of an MRI scanner 14. As shown, the patient 10 has been fitted with the anti claustrophobic glasses or goggles 20 of the present invention. The goggles 20 include a mirror element 22 which, as seen, has redirected the view of the patient to a target 24 which is mounted on a wall 26 exterior to the scanning cavity 12.

For purposes of medical diagnosis, the patient 10 generally must remain wholly within the cavity 12 for periods of time in excess of 20 to 30 minutes, which can be quite unnerving for persons who are uncomfortable in closely confined areas. The present invention permits the patient's vision to be redirected to a preselected scene or target 24 which has been found to be comforting and palliative.

As seen in FIGS. 2 and 3, the present invention includes a frame member 30 of electromagnetically inert material. The frame member 30 includes a lens holding front portion 32 and side portions 34 to which a headband 36 can be attached. The front portion 32 includes lens holding apertures 38 in which lenses 40 can conveniently be inserted or removed. The lenses 40 can be selected for each patient's optical needs.

Mounted upon the side portions 34 of the frame member 30 are a pair of plates 42. A mirror element 44 having integral adjusting handles 46 extending from the ends thereof is mounted through elastomeric grommets 48 carried at the forward end of the plates 42. The grommets 48 frictionally hold the mirror element 44 in a rotational orientation as determined by a positioning of the handles 46.

The mirror element 44 is provided with a limited amount of travel toward and away from the frame member 30 through the use of slots 50 in the plates 42. Magnetically inert fasteners 52, through the slots 50 hold the plates to the side portions 34.

In use, the patient's vision is checked and lenses 40 with the appropriate correction are inserted into the lens holding apertures 38. These apertures 38 are sized so that the lenses 40 can be easily snap fitted in and out of the frame member 30. The patient 10 is then fitted with the frame member 30 and the headband 36 is adjusted so that the device is snug and comfortable.

With the patient 10 supine on the movable element of the scanner 14, the mirror element 44 is angled using the adjusting handles 46 until the patient 10 can see the "target" 24 or scene, which has been chosen to provide a familiar scene for the patient to view over the period of the scan.

While the device has been shown in use with an MRI scanner, the goggles of the present invention can be utilized in any situation in which a patient is in an environment where the view to the "front" is blocked or occluded and the situation tends to cause anxiety or discomfort. For example, a dental patient undergoing a prolonged procedure could, using the present invention, have his view redirected to a television set or a poster that would distract and ameliorate anxieties.

Other environments, such as radiation devices or CAT scanners and the like, could be envisioned in which the present invention could be useful, inasmuch as the easy replacement of lenses permits virtually any patient to utilize the device with an acceptable optical correction. This permits virtually any remote scene to be viewed with clarity and detail.

Thus there has been shown and described a novel anti-claustrophobic goggle which can be used in the unique environment of an MRI scanner, but which also has utility in less challenging situations. The device is fabricated of magnetically inert elements and is easily adjusted to redirect the wearer's line of sight to a predetermined scene that can be conveniently placed, out of the wearer's normal viewing direction which may be otherwise occluded.

Other embodiments and variations can be envisioned without departing from the teachings of the present invention and, accordingly, the invention should be limited only by the scope of the claims appended hereto.

What is claimed as new is:

1. For use in the environment of an MRI scanner by a plurality of patients subject to claustrophobic type fears, the combination of:
   (a) non magnetic lens holding means adapted to be worn by a patient;
   (b) a set of pairs of lenses sized to easily press fit in and out of said lens holding means, each of said pairs of lenses having different optical correction so that a pair of lenses can be selected which approximate the correction required by each patient wearing said lens holding means;
   (c) bracket means attached to said lens holding mean for mounting a mirror in the patient's direct line of sight; and
   (d) mirror means rotationally mounted in said bracket means for redirecting the patient's vision in a direction that is substantially unobstructed by the scanner to a remote, preselected target, said mirror means including handle means extending through said bracket means for rotationally adjusting said mirror means to redirect the patient's sight path, said handle means being mounted in elastomeric grommet means in said bracket means so that an adjustment, once made, is frictionally held in place,
   whereby the elements of the combination are made of materials that do not affect the MRI scan but allow a patient whose direct vision is obscured by the scanner to view a scene other than the scanner.

2. The apparatus of claim 1, above, in which said bracket means are attached to said lens holding means by fastening elements through elongated slots in said bracket means, whereby the separation and angle of said mirror means can be adjusted.

3. The apparatus of claim 1, above, further including head encircling means attached to said lens holding means for adjustably holding the claimed combination in position on a wearer's head.

4. The apparatus of claim 3, above, wherein said head encircling means includes an elasticized strap member of adjustable length.

5. The apparatus of claim 1, above, wherein said mirror means include a clear plastic substrate and a reflective coating deposited thereon.

6. For use in an environment subjecting a patient to claustrophobic type fears, the combination of:
   (a) lens holding means adapted to be worn by a plurality of patients;
   (b) a set of pairs of lenses sized to easily press fit in and out of said lens holding means, each of said pairs of lenses having different optical corrections so that a pair of lenses can be selected which approximate the correction required by each patient wearing said lens holding means;
   (c) bracket means attached to said lens holding means for mounting a mirror in a patient's direct line of sight; and
   (d) mirror means including a plane mirror rotationally mounted in said bracket means for redirecting the patient's vision in a direction that is substantially unobstructed to a remote, preselected target, said mirror means including handle means extending through said bracket means for rotationally adjusting said mirror means to redirect the patient's sight path, said handle means being mounted in elastomeric grommet means in said bracket means so that an adjustment, once made, is frictionally held in place,
   whereby the wearer is afforded a line of sight to a scene capable of having a calming effect to ameliorate claustrobic type fears.

7. The apparatus of claim 6, above, in which said bracket means are attached to said lens holding means by fastening elements through elongated slots in said bracket means, whereby the separation and angle of said mirror means can be adjusted.

8. The apparatus of claim 6, above, further including head encircling means attached to said lens holding means for adjustably holding the claimed combination in position on a wearer's head.

9. The apparatus of claim 8, above, wherein said head encircling means includes an elasticized strap member of adjustable length.

10. The apparatus of claim 6, above, wherein said mirror means include a clear plastic substrate and a reflective coating deposited thereon.

11. The apparatus of claim 6, above, wherein all of the components of said combination are made of non magnetizable, non ferrous materials to which MRI scanners and the like are insensitive, whereby a patient who is substantially surrounded by MRI scanning equipment and whose direct vision is otherwise obscured by the MRI scanning equipment, is provided with an optical path to a remote scene thereby avoiding potential claustrophobic reactions.

* * * * *